US012765967B2

(12) United States Patent
Carriere Lluch

(10) Patent No.: US 12,765,967 B2
(45) Date of Patent: Oct. 20, 2026

(54) ADDITIVE MANUFACTURING FOR ORTHODONTIC TREATMENTS

(71) Applicant: ORTHODONTIC RESEARCH AND DEVELOPMENT S.L., Barcelona (ES)

(72) Inventor: Luis Carriere Lluch, Barcelona (ES)

(73) Assignee: ORTHODONTIC RESEARCH AND DEVELOPMENT S.L., Barcelona (ES)

( * ) Notice: Subject to any disclaimer, the term of this patent is extended or adjusted under 35 U.S.C. 154(b) by 85 days.

(21) Appl. No.: 18/710,898

(22) PCT Filed: Nov. 16, 2022

(86) PCT No.: PCT/EP2022/082099
§ 371 (c)(1),
(2) Date: May 16, 2024

(87) PCT Pub. No.: WO2023/088945
PCT Pub. Date: May 25, 2023

(65) Prior Publication Data
US 2025/0032215 A1 Jan. 30, 2025

(30) Foreign Application Priority Data
Nov. 17, 2021 (EP) .................................... 21383042

(51) Int. Cl.
*A61C 7/00* (2006.01)
*A61C 7/16* (2006.01)
(Continued)

(52) U.S. Cl.
CPC ................ *A61C 7/002* (2013.01); *A61C 7/16* (2013.01); *A61C 13/34* (2013.01); *G06T 19/20* (2013.01);
(Continued)

(58) Field of Classification Search
None
See application file for complete search history.

(56) References Cited

U.S. PATENT DOCUMENTS

2004/0029068 A1 2/2004 Sachdeva et al.
2004/0229183 A1 * 11/2004 Knopp .................... A61C 7/00 433/213
(Continued)

OTHER PUBLICATIONS

International Search Report and Written Opinion mailed Feb. 10, 2023, for International Application No. PCT/EP2022/082099, 10 pages.

*Primary Examiner* — Kyle Zhai
(74) *Attorney, Agent, or Firm* — SQUIRE PATTON BOGGS (US) LLP

(57) ABSTRACT

Computer implemented methods for generating an input file for a 3D printer, the methods comprising visualizing a virtual model of a patient's teeth on a display, visualizing a predefined virtual orthodontic treatment device on the display and adapting a shape of the predefined virtual orthodontic treatment device in response to user input. The method then comprises generating an input file for a 3D printer based on the adapted virtual orthodontic treatment device. The present disclosure further relates to computing systems, and computer programs and methods for 3D printing orthodontic treatment devices.

16 Claims, 5 Drawing Sheets

(51) Int. Cl.
*A61C 13/34* (2006.01)
*G06T 19/20* (2011.01)
*G16H 40/63* (2018.01)

(52) U.S. Cl.
CPC ......... *G16H 40/63* (2018.01); *G06T 2210/41* (2013.01); *G06T 2219/2021* (2013.01)

(56) References Cited

U.S. PATENT DOCUMENTS

| | | | | |
|---|---|---|---|---|
| 2009/0017410 | A1* | 1/2009 | Raby | A61C 7/146 433/2 |
| 2010/0106465 | A1* | 4/2010 | Sporbert | A61C 7/00 703/1 |
| 2012/0281013 | A1* | 11/2012 | Mahdavi | G06T 19/00 345/619 |
| 2017/0049534 | A1 | 2/2017 | Soo et al. | |
| 2018/0267509 | A1* | 9/2018 | Grapsas | G05B 19/19 |
| 2019/0046298 | A1* | 2/2019 | Cinader, Jr. | A61C 7/14 |
| 2019/0333622 | A1* | 10/2019 | Levin | G16H 50/70 |
| 2020/0060789 | A1* | 2/2020 | Sachdeva | A61C 7/08 |
| 2020/0401104 | A1* | 12/2020 | Griffin, III | B33Y 80/00 |

* cited by examiner

ADDITIVE MANUFACTURING FOR ORTHODONTIC TREATMENTS

CROSS-REFERENCE

The present application is a National Stage filing under 35 U.S.C. § 371 of International Patent Application No. PCT/EP2022/082099, filed Nov. 16, 2022, which claims the benefit of and priority to European Patent Application No. EP21383042.5 filed Nov. 17, 2021, the contents of all of which are hereby incorporated by reference in their entireties for all purposes.

The present application claims the benefit of EP21383042.5 filed on Nov. 17, 2021.

The present disclosure relates to orthodontic treatment devices, and methods. More particularly, the present disclosure relates to methods and systems for using additive manufacturing of devices that may be used in orthodontic treatments. The present disclosure also relates to computer programs for preparing electronic archives used in additive manufacturing.

BACKGROUND

The correction of dental irregularities and malocclusions by applying controlled forces to the teeth has become commonplace. Orthodontists offer a wide range of treatment options to straighten crooked teeth, fix irregular bites and align the jaws correctly. There are many ways to adjust malocclusion. Sometimes teeth are extracted to aid the orthodontic treatment.

An orthodontic treatment will typically start with a thorough examination of a patient's malocclusion. An orthodontist may inspect a patient's teeth from various angles and positions, X-rays may be used, plaster models of teeth may be made. Also the use of scanners which can generate a 3D virtual model of a patient's jaws, teeth and gums are known.

Based on the diagnosis, and based on a dialogue with the patient, an orthodontic treatment plan may be made. In such a treatment plan, the use of different types of orthodontic treatment devices may be foreseen e.g. brackets, headgear, expanders, distalizers and others.

An orthodontist may order the orthodontic devices from a manufacturer of choice. While some orthodontic devices may allow some limited adaptation by the orthodontist in situ to adapt for the specific malocclusion of a patient, most devices cannot be adapted and may be delivered in only a few standard sizes. In reality, every patient has a unique set of teeth and a unique malocclusion and therefore, using standard sized devices is suboptimal.

3D printing, or additive manufacturing, is the construction of a three-dimensional object from a CAD model or a digital 3D model. The term "3D printing" can refer to a variety of processes in which material is deposited, joined or solidified under computer control to create a three-dimensional object, with material being added together (such as plastics, liquids or powder grains being fused together), typically layer by layer.

3D printing techniques were originally considered suitable only for the production of functional or aesthetic prototypes. However, the precision, repeatability, and material range of 3D printing have increased considerably and now represent viable manufacturing processes in a wide range of industries.

One of the key advantages of 3D printing is the ability to produce very complex shapes or geometries. Fused deposition modelling (FDM), which uses a continuous filament of a thermoplastic material, is the most common 3D printing process nowadays.

3D printing offers interesting advantages and possibilities in the manufacture of orthodontic treatment devices as well. These devices can potentially be manufactured to be adapted precisely according to the needs of the patient or the treatment.

3D printing to this day has however had limited application in orthodontics. The exception is the use of so-called aligners, i.e. shells covering an arch of teeth. Transparent or translucent aligners commercialized under the name Invisalign® and under other names have become popular due to its pleasant design as compared to traditional brackets. The treatment with aligners includes designing a treatment path for a complete arch of teeth, wherein the teeth undergo a movement from the original position to a final desired position. Then, a number of consecutive intermediate positions in between the original and the final position for the teeth are determined, including movements of teeth that may include rotation about a root, torsion, in-out displacement, and mesial-distal displacement. A series of shells (dental splints) is then provided to the patient. These shells correspond to the arch of teeth in their intermediate positions. The shells apply corrective forces to the arch of teeth (when fitted onto the teeth), because the shell is shaped according to the next intermediate position. Each of the shells is used during a period of time, e.g. one or a few weeks. Once the teeth have assumed the desired position, a shell corresponding to the next intermediate position is to be fitted. This process goes on until ultimately, the teeth reach their final desired position.

These aligners may be manufactured using 3D printing. I.e. a 3D virtual model of a patient's teeth is obtained, and the aligners are adapted to the teeth of the individual patient. 3D printing is also known to be used for the manufacture of indirect bonding trays. In both cases, shells are manufactured and completely adapted to a specific patient.

However, beyond these applications, 3D printing has hardly been used by orthodontists to this date. In an article by Ghislanzoni et al. "Digital Lab Appliances: The Time Has Come", published in 2020 in the Journal of Clinical Orthodontics, it is argued that digital version of traditional laboratory-produced appliances are rarely presented in literature and when they are, they are labelled as experimental. The same article signals that there is a vast potential in digital orthodontics.

In a recent development, described in WO 2021/091810 A1, a software is provided which allows a user (orthodontist) to select an orthodontic appliance from a catalogue. The selected orthodontic appliance may be composed by combining several predefined objects. A plurality of appliances can be ordered at the same time. The ordered appliances are then 3D printed. The 3D printing is carried out based on predetermined data files generated remotely. An objective of the disclosure is to reduce overhead for orthodontists Document US 2017/0049534 A1 discloses a method of making a customized orthodontic bracket and in particular to a method in which a pre-manufactured physical bracket body is combined with three-dimensionally built-up bracket base. Document US 2004/0029068 A1 discloses a method and workstation for orthodontic treatment planning of a patient.

The present disclosure in various examples provides methods, and systems that allow to expand the use of 3D printing in orthodontic treatments. This can allow well-known orthodontic treatment devices to be made to fit an individual patient's needs.

SUMMARY

In a first aspect, a computer implemented method for generating an input file for a 3D printer is provided. The method comprises visualizing a virtual model of a patient's teeth on a display and visualizing a predefined virtual orthodontic treatment device on the display. The method comprises adapting a shape of the predefined virtual orthodontic treatment device in response to user input and at least partially based on the virtual model of the patient's teeth and generating an input file for a 3D printer based on the adapted virtual orthodontic treatment device.

In accordance with this aspect, a method is provided which allows and facilitates 3D printing of a wide variety of orthodontic treatment devices. The method provides a balance between an efficient manufacturing method and the ability to adapt devices in detail to specific individual malocclusions. Instead of having to generate a model of an orthodontic treatment device from scratch, a virtual orthodontic treatment device has been predefined. A user can then adapt the predefined virtual orthodontic treatment device to adapt to or fit a virtual representation of a patients' teeth.

As opposed to some prior art initiatives, the input file for the 3D printer is based to some extent on the virtual model of the patient's teeth. The input file for the 3D printer can therefore not be wholly predefined and is generated in the moment. Objects within the virtual orthodontic treatment device may have been predefined and therefore input files for a 3D printer may therefore be generated using e.g. merging predefined code portions.

"Predefined" may herein be regarded as at least partially independent from any patient, malocclusion, tooth or set of teeth. I.e. independently of the specific malocclusion, position of teeth and jaws etc. in a patient, a starting point of a virtual model of the orthodontic treatment device is provided. This virtual model may then be adapted to fit to a specific tooth or patient, but the starting point is not derived from any measurement, examination or image of a specific patient.

An orthodontic treatment device may herein be regarded as a device that is used to exert forces and/or movements on a tooth or a set of teeth. More particularly, orthodontic treatment devices as used herein are meant to include devices that are bonded or otherwise fixed to an outer surface or part of an outer surface of one or more teeth. Dental prostheses are herein not considered as orthodontic treatment devices. Also, within the scope of the present disclosure it is not the aim to adapt or polish the surface of an existing tooth, rather the scope is to adapt an orthodontic treatment device to e.g. a perimeter or surface of a tooth.

A virtual orthodontic treatment device may herein be regarded as a digital version of an orthodontic treatment device. A virtual device may be displayed on a suitable display, and may be digitally or "virtually" manipulated through a suitable electronic user interface. Such an interface may be or include a tactile display, a computer keyboard, a computer mouse, or other.

A virtual model of a patient's teeth may herein be regarded as a digital version of one or more teeth of a patient. Typically, a virtual model may include both complete arches of a patient's teeth, and may include part of the patient's jaws and gums as well. A virtual model of patient's teeth may be visualized on a display and may be manipulated through a suitable electronic user interface. The virtual model may have different formats, and be purely graphical, or in some examples may be such that it can be used in e.g. calculations, simulations involving finite elements. The virtual model of a patient's teeth may be a digital solid model (3D model), a polygon mesh, a NURBS model or similar.

A virtual graphic model may include a graphical mathematical coordinate-based representation of an object (in this case, one or more of a real patient's teeth) in three dimensions via specialized software by manipulating edges, vertices, and polygons in a simulated 3D space. 3D models represent a physical body using a collection of points in 3D space, connected by various geometric entities such as triangles, lines, curved surfaces, etc. Being a collection of data (points and other information), 3D models can be created manually, algorithmically (procedural modeling), or by scanning. Their surfaces may be further defined with texture mapping.

Regardless of the definitions and elements used for the virtual model of the patient's teeth, since the teeth of the patient are mathematically defined in one way or another, a user may indicate precise points, surfaces or edges of the virtual model that are to be taken into account in the adaptation of the virtual treatment device. E.g. a point, multiple points, a surface or edge may be selected by a user, and the virtual orthodontic treatment device may be adapted to it by changing a curvature, a length, a width or other.

In some examples, the predefined virtual orthodontic treatment device may be selected from a library of predefined virtual orthodontic treatment devices. Such a library of predefined virtual orthodontic treatment devices may comprise e.g. one or more of: orthodontic brackets, distalizers (such as Carriere Motion™ devices), expanders, Herbst® appliance, retainer, separators, distal jet appliance, lingual arch, transpalatal arch and bite plates or any other suitable orthodontic appliance that an orthodontist may wish to use in an orthodontic treatment. The predefined virtual orthodontic treatment devices may be partly customizable, i.e. some characteristics, features may be changed to adapt an orthodontic treatment device to a specific patient's set of teeth.

In some examples, user input may also include a selection of the 3D printer to be used for 3D printing, and or material to be used. The selection of material may include selecting from a plurality of different resins, or powders.

In some examples, the predefined virtual orthodontic treatment devices may comprise an adaptable portion which can be adapted in response to user input, and a less adaptable portion which cannot be adapted in response to user input or can be adapted less freely than the adaptable. A less-adaptable portion may be non-adaptable or adaptable to a limited extent.

In some examples, the predefined virtual orthodontic treatment devices may comprise an adaptable portion (adaptable in response to user input), a partly adaptable portion (with limited adaptability) and a non-adaptable portion.

The predefined virtual orthodontic treatment devices may have a certain predefined and unmodifiable portion. For example, the non-adaptable portion may comprise a joint between elements, and/or an active element of the orthodontic treatment device. A joint may be any connection that allows limited movement between two elements and may be e.g. a hinge, a bearing, a guide, a slide or other. An active element may herein be regarded as a force generating element e.g. involving a spring, a resilient or elastic element or a joint which is such that in use a force is exerted by one element onto another.

In examples, non-adaptable portions of the virtual models of orthodontic treatment devices may include parts of the orthodontic treatment devices that require manufacturing with very low tolerances (i.e. with very high precision).

Non-adaptable portions may include specifically areas or portions of an orthodontic treatment device that are important for orthodontic outcome, or for the proper functioning of a device, and/or portions that require precision in manufacturing and portions that in use collaborate with other orthodontic appliances.

In some examples, the adaptable portion comprises a base or base surfaces for anchoring the orthodontic treatment device to the patient's mouth, and/or a connector. For example, for a bracket or molar tube, a size and shape of a base surface or band to be cemented on a tooth may be adapted by a user, whereas e.g. a lock, a slot for an archwire, or a hook of the bracket may be predefined and do not need to be created. In examples, one or more these elements cannot be amended by a user. In a further example, in the case of a Carriere Motion™ distalizer, a ball and socket joint may be predefined as part of the virtual orthodontic treatment device. The parts of the Motion™ distalizer that may be modified by a user and adapted to a patient's specific malocclusion may include the size, and/or base surfaces of the distal and mesial elements, as well as a length of an arm connecting the distal and mesial elements.

Partly adaptable portions may only be partially adapted, e.g. they may only be scaled and/or rotated and/or repositioned with respect to other portions of the virtual orthodontic treatment device.

In some examples, the method may further comprise receiving the virtual model of the patient's teeth. The virtual model may be generated in a different device, computer system or a different software. In other examples, the method may comprise generating the virtual model of the patient's teeth.

In some examples, the method may further comprise virtually attaching the adapted or the predefined virtual orthodontic treatment device to the virtual model of the patient's teeth. Optionally, the method may further comprise simulating an orthodontic treatment based on the use of the adapted virtual orthodontic treatment device or calculating a movement or force exerted by the orthodontic treatment device on a tooth or set of teeth. In this case, an orthodontist or other professional may design an orthodontic treatment device and simulate the results of the treatment.

Based on the simulation, the user may determine that the design of the orthodontic treatment device is satisfactory or not. If not, the user may further adapt the virtual orthodontic treatment device. For example, an orthodontist may decide to select a different type of bracket, to modify an inclination of an archwire slot, to adapt a width of an expander, or to fit an orthodontic treatment device to a different tooth, to an additional tooth or to a different set of teeth.

In some examples, the method may further comprise verifying manufacturability or feasibility of the adapted virtual orthodontic treatment device. For example, based on the material (e.g. resin) desired for 3D printing, or based on the 3D printer that is to be used, there may be limitations as to the designs that can be manufactured. Before, during or after generating the input file for the 3D printer, manufacturability may be checked. A warning may appear on a screen in case manufacturing is deemed complex or impossible. Alternatively, a change of material or a change of 3D printer may be suggested on the screen in order to ensure manufacturability.

In a further aspect, a computer program is provided which comprises instructions which, when the program is executed by a computer, cause the computer to carry out any of the methods disclosed herein. In yet a further aspect, a computer readable medium having the computer program stored thereon is provided. In a further aspect, a carrier signal carrying the computer program is provided.

In yet a further aspect, a computer system is provided which comprises a memory and a processor, wherein the processor is configured to carry out the method according to any of the examples disclosed herein.

In yet a further aspect, a method for manufacturing an orthodontic treatment device is provided. The method comprises generating a virtual model of a patient's teeth; and displaying the virtual model of the patient's teeth on a display. The method further comprises selecting a virtual orthodontic treatment device from a library of predefined virtual treatment orthodontic treatment devices and visualizing the selected virtual orthodontic treatment device on the display. The method further comprises adapting a shape of the selected virtual orthodontic treatment device to adapt to the virtual model of the patient's teeth, generating an input file for a 3D printer based on the adapted virtual orthodontic treatment device and 3D printing the orthodontic treatment device according to the generated input file.

Adapting the shape of the selected virtual orthodontic treatment device may at least be partially based on the virtual model of the patient's teeth.

In some example, the user input for adapting a shape of the predefined virtual orthodontic treatment device may include a selection of one or more of a point, a line or a surface of the virtual model of the patient's teeth.

BRIEF DESCRIPTION OF THE DRAWINGS

Non-limiting examples of the present disclosure will be described in the following, with reference to the appended drawings, in which.

DETAILED DESCRIPTION OF EXAMPLES

Figure 1:
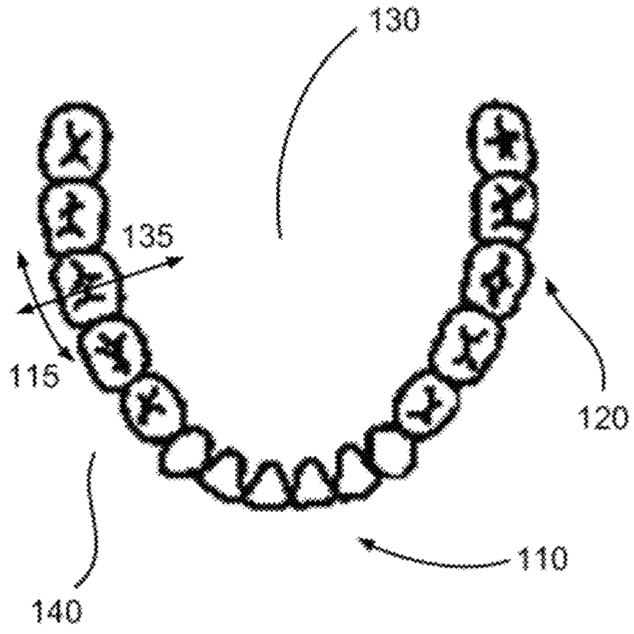
FIG. 1 schematically illustrates some terminology of the orthodontics field as employed in the present disclosure.

FIG. 1 schematically illustrates the arrangement of teeth in the lower jaw (mandible). A front portion of the mouth 110 may be referred to as a mesial region. A rear portion of the mouth 120 may be referred to as a distal region. In orthodontics, mesial and distal are terms used to refer to something being respectively closer to and further away from a central midline of the arch of teeth.

In the distal region of the mouth, the molar zone may be found. The molar zone may include a first molar, a second molar and possibly a third molar ("wisdom tooth"). An inner portion of the mouth behind the teeth 130 may be referred to as a lingual region (a region in which the tongue is located). An outer portion of the mouth 140 may be referred to as a labial region (a region in which the lips are located). A mesial-distal direction 115 with respect to a specific tooth (first molar) has been schematically indicated in FIG. 6. Also indicated in FIG. 6 is a lingual-labial direction 135 with respect to the same tooth. This terminology will be adhered to in the present disclosure. Instead of "lingual-labial", reference may also be made to "lingual-buccal". Finally, the occlusal-gingival direction is perpendicular to both the distal-mesial and to the buccal-lingual direction. The gingival region of a tooth is the region of the tooth covered by or in the vicinity of the gum, whereas the occlusal region is at the opposite end.

Even though a mandible is illustrated in this particular figure, it should be clear that the same terminology applies to the maxilla.

Figure 2:
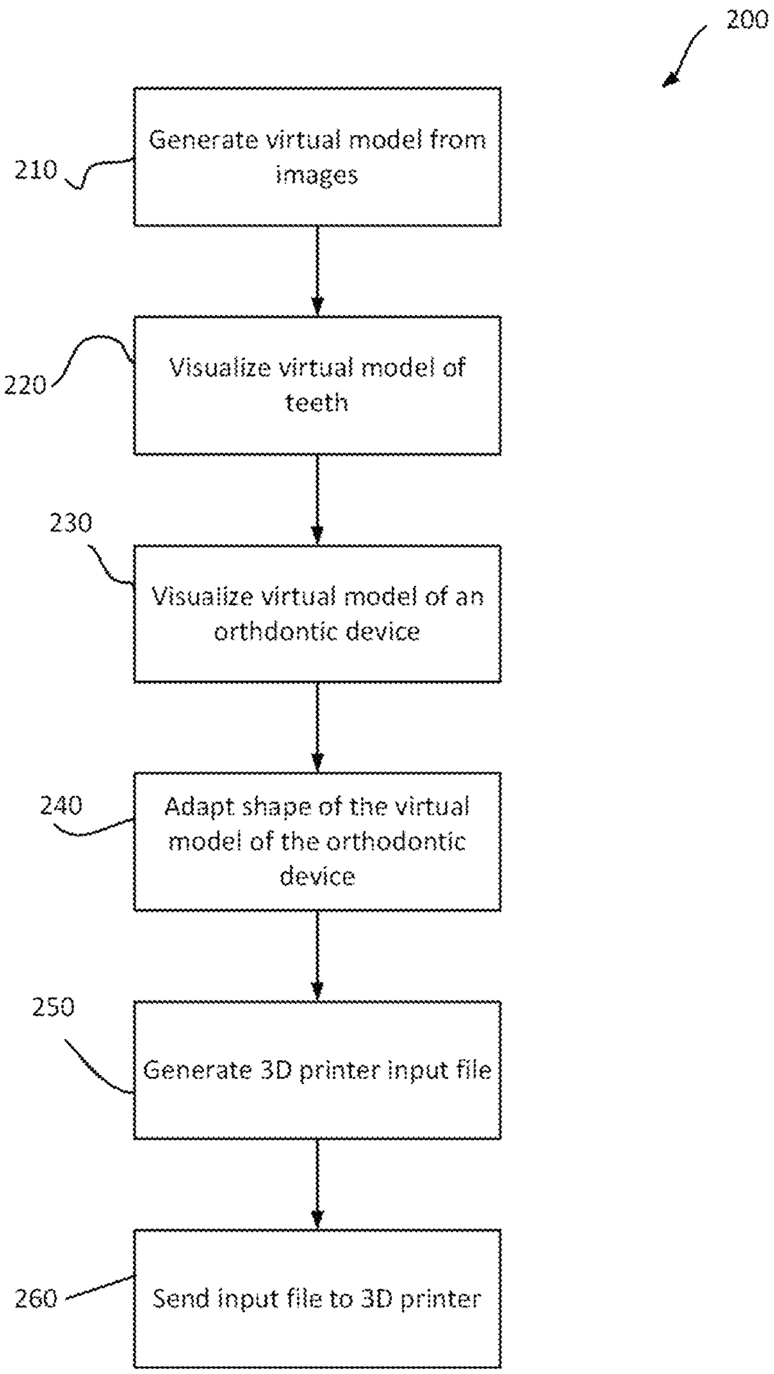
FIG. 2 schematically illustrated a method for generating an input file for a 3D printer according to a first example.

FIG. 2 schematically illustrates a method 200 for generating an input file for a 3D printer according to a first example. A computer implemented method 200 for generating an input file for a 3D printer is shown. The method 200 comprises, at block 220, visualizing a virtual model of a patient's teeth on a display and visualizing a predefined virtual orthodontic treatment device on the display at block 230. The method further comprises, at block 240, adapting a shape of the predefined virtual orthodontic treatment device in response to user input. Once a user has determined a suitable shape for the orthodontic treatment device, the method comprises, at block 250, generating an input file for a 3D printer based on the adapted virtual orthodontic treatment device.

Optionally, at block 260, the method may comprise sending the input file to a suitable 3D printer.

The virtual model of the patient's teeth may be regarded as a digital version of a patient's set of teeth. The virtual model may particularly be a three-dimensional model, which may be computer generated and may be based on a plurality of images of the patient's teeth, at block 210. A 3D scanner such as an intraoral scanner or a cone beam computed tomography (ct) scanner may be used to generate such images. The scanner may be communicatively coupled to a computer system, either wireless or through cable. The computer system may have suitable software to generate a virtual model of the teeth. The virtual model may be or include a graphic model.

The use of a virtual model of teeth allows visualization of the malocclusion, both for the patient and for the professionals treating the patient. The use of the virtual model of teeth allows for a continued and guided interaction process of an orthodontist with the malocclusion and the treatment device(s) selected for the treatment.

The virtual model may further be used to simulate a treatment, or to calculate a suitable treatment trajectory. Software capable of performing these calculations and simulations is known in the art.

Simulations may be based on a finite element method (FEM). A finite element model may be part of or derived from the virtual model of the teeth of the patient. E.g. the virtual model of a patient's teeth may include definitions of collections of points, connected by vertices, edges, lines, curved surfaces etc. Based on the definition of the collection of points, a finite element model may be generated.

The use of FEM is known in the art of orthodontics. The finite element calculations may be carried out in the same computer system or computer program or in a separate dedicated system or application.

At block 220, the virtual model of the teeth may be visualized on a display. The display may be a tactile screen, television, standard computer monitor or any other suitable display.

At block 230, also a virtual model of an orthodontic treatment device may be visualized on the same display. The virtual model of the orthodontic treatment device may be regarded as a digital 3D version of a real orthodontic treatment device. The physical orthodontic treatment device may be configured to be attached, cemented or otherwise bonded to a surface of a tooth of patient or a set of teeth.

The orthodontic treatment device may include a base surface configured to be attached to a lingual or labial surface of a tooth. Such a base surface may include dovetail grooves or other elements to increase friction once cemented. In other examples, an orthodontic treatment device may comprise a first base surface for attachment to a surface of a first tooth, and a second base surface for attachment to a surface of another tooth. In yet other examples, an orthodontic treatment device may include more than two base surfaces for attachment to more than two surfaces, e.g. surfaces of teeth.

The orthodontic treatment device may also include a so-called "band". A band is typically a thin metal ring, usually of stainless steel, which serves to secure a treatment device to a tooth. The band may be closely adapted to fit the contours of each individual tooth and then cemented into place. In other examples, specifically when the orthodontic treatment device is to be attached at multiple locations e.g., around multiple teeth, the treatment device may include two or more bands.

The predefined virtual orthodontic treatment device may be selected from a library of predefined virtual orthodontic treatment devices. A library may herein be regarded as a collection or database of predefined virtual orthodontic treatment devices, the virtual orthodontic treatment devices all representing real orthodontic treatment devices that may be manufactured with 3D printing. The library may have any suitable menu structure to allow a professional to select a suitable orthodontic treatment device.

The library may contain a number of predefined virtual models of devices that can be manufactured by a 3D printer. The library of predefined virtual orthodontic treatment devices may comprise e.g. one or more of: orthodontic brackets (self-ligating or non self-ligating), distalizers (e.g. Carriere Motion™ distalizers or other), expanders, Herbst® appliance, retainer, separators, distal jet appliance, lingual arch, transpalatal arch and bite plates. The library may in some examples have a hierarchical menu structure for selecting the desired appliance, e.g. a user may first select "brackets", then select "self-ligating brackets" and in response to the user's input a listing of available self-ligating brackets may be displayed. In such an example, a list of self-ligating brackets may include different brackets with e.g. different archwire retention mechanisms, for different archwire sizes, with different archwire positions, or orientations and e.g. brackets made of different materials.

Such a library may also contain predefined base surfaces with different textures (dovetail, protrusions, spikes or other) for cementing on teeth. A user may select specific textures for selected treatment devices.

At block 240, the shape of the virtual model of the orthodontic treatment device may be adapted based on user input. I.e. a user may use a computer keyboard, a computer mouse, a tactile display or other user interface to change a shape of the virtual model of the orthodontic treatment device, particularly to adapt it to the virtual teeth of the patient and/or to make it suitable for the specific treatment plan for the patient. In an example, the size of a virtual model may be adapted to fit a patient's tooth, or to span a length from a mesial tooth such as a canine to a molar, to span the distance between a tooth on one side of the arch to a tooth on the other side of the arch (i.e. across the palate). In further examples, a base surface or band for cementing to a tooth surface may be adapted to the surface of the virtual model of the specific patient.

As a user gives input to adapt the virtual model of the orthodontic treatment device, the resulting adapted model of the treatment device may be visualized on the display e.g. in real-time.

Adapting the shape of the virtual model of the orthodontic treatment device may additionally or alternatively include an automatic calculation and adaptation of a portion of the virtual orthodontic treatment to the virtual model of a patient's teeth. For example, a user may select and indicate a tooth in the virtual model to which the orthodontic treatment device is to be bonded (for the real, physical, orthodontic treatment) and based on the model of the patient's teeth, the computer (program) may calculate a suitable band or base surface to be fitted to or around a patient's tooth. A user may also indicate points in the virtual model where treatment devices are to be cemented, or otherwise mounted or points that are to determine a length or other dimensions of a treatment device.

The system may be adapted to calculate e.g. distances between points, edges, surfaces of the virtual model of the patient's teeth. Such a distance may then be used to determine e.g. a length, width of height of a virtual orthodontic treatment device (or components of such a device). The system may also be adapted to calculate a radius of curvature of a user selected surface of the virtual model of the patient's teeth, an angle between two user selected points of the virtual model of the patient's teeth, and use these data in the adaptation of the virtual orthodontic treatment device.

Input from a computer keyboard may e.g. include entering coordinates of points, identification of edges or specific points of a virtual model of the teeth, a scale factor, or input relating to dimensions or size of an orthodontic treatment device or components of such a device. Input from a mouse or tactile display may include the same and may also include e.g. selection of a specific size or dimensions from a drop-down menu, or a user adding and drawing lines or surfaces. It should be clear that user input from various devices and sources may also be combined.

In examples, the predefined virtual orthodontic treatment devices may comprise an adaptable portion which can be adapted in response to user input, and a less adaptable portion. The less adaptable portion may be adapted only to a limited extent (e.g. only scaled, while maintaining aspect ratio, or rotated while maintaining a fixed connection with other parts of the virtual orthodontic treatment device) or may be a non-adaptable portion which cannot be adapted in response to user input.

Certain portions of the device may not be amended. Portions of the virtual orthodontic treatment device may be "locked" or frozen". This may be done to avoid allowing a user to generate a shape that is too complicated to manufacture or a shape that would render the orthodontic treatment device less useful or less efficient. Portions of the virtual orthodontic treatment device that may not be adapted may include parts that require very precise manufacturing, i.e. relatively low tolerances.

Other portions of the device may be easily amended by a user. E.g. a mounting surface or other element that is to be bonded to a tooth may be adjusted by making the mounting surface larger or smaller, wider or thinner, longer or shorter, more or less curved. The need to have an orthodontist or other professional design an orthodontic treatment device completely from scratch can be avoided. Not every individual detail of a bracket or distalizer or expander needs to designed. With the method proposed herein, an orthodontist can have a library of predefined treatment devices and he/she can customize them to specific needs.

In some examples, a non-adaptable portion of an orthodontic treatment device may comprise a joint, and/or an active element of the orthodontic treatment device. Joints are connections between bodies that allow movement of the bodies with respect to each other. Joints in orthodontic treatment devices may include ball-socket joints, hinges, bearings, sliding joints and other. Joints allowing bodies to move with respect to each other in use, are generally harder to manufacture with 3D printing. Predefined joints in predefined virtual orthodontic treatment devices that can be manufactured may therefore be part of the design that cannot be changed by a user. Joints in orthodontic treatment devices may include hinges, rotational joints, or sliding joints.

In the case of an orthodontic bracket for example, a base or bonding surface of a bracket may be freely adaptable, and in particular may be adapted to a surface of a tooth to which the bracket is to be bonded. In some cases, the structure surrounding the archwire slot may form part of the non-adaptable or locked portion of the virtual bracket, i.e. it cannot be modified by a user. In other cases, the archwire slot and surround structure may form part of the less adaptable portion of the virtual model of the bracket (e.g. the archwire slot may be scaled or rotated, but the inside of the slot may not be modified). Further portions of the bracket that might be changed by a user may include the orientation of the bracket body with respect to its base surface.

Active elements or force generating elements, such as springs, are further elements that may be complicated to manufacture with 3D printing. Such elements may also belong to the non-adaptable portions of some of the virtual devices defined in the library.

In some examples, the (freely) adaptable portion comprises a base or band for anchoring the orthodontic treatment device to the patient's mouth, and/or a connector. As mentioned before, connecting portions, surfaces that are cemented to teeth, bands that may be fitted around teeth may be easily adapted to the specific shape of the patient's teeth by using the virtual model of the teeth.

In some examples, predefined virtual orthodontic treatment devices configured to be bonded to one or more teeth of a patient may be configured to be adapted in an occlusal-gingival plane and or a mesial-distal plane, and are configured not to be adapted in a buccal-lingual plane. In the buccal-lingual plane, the active functional elements like locks, hooks, force generating elements may be defined. In some implementations, in order to have virtual devices that can effectively be 3D printed and maintain their efficiency in use, such elements may not be amended.

In some examples, a virtual model of an orthodontic treatment device may include separate predefined virtual objects. In examples, the positions and/or orientations of the virtual objects within a single virtual device may be changed, but their shape may not.

Once an orthodontist or other professional has designed the orthodontic treatment device according to the specific needs of a patient or adapted to the teeth of a specific patient, an input file for a 3D printer may be generated. E.g. a user may select freeing the design and entering a command for generating the input file.

In some examples, the input file for the 3D printer is in one of the following formats: .stl, .obj, .gcode, .amf, .vrml, .ply, .fbx, .3mf. Any suitable format may be chosen depending on the selected printer, and depending on the applications or functionalities used to adapt the shape of the virtual orthodontic treatment devices.

STL is currently the most common file format when 3D printing. STL is a standard file format that can interface between most CAD software and 3D printers. STL files can contain a triangular representation of a 3-dimensional object.

.OBJ is the second most common file format used in 3D printing. It is widely supported by 3D printers. This file is similar to .STL in that it contains 3D geometry information, such as vertex normals, geometric vertices, polygonal faces and texture coordinates.

.gcode, otherwise known as .g or .gco, is the file extension for files containing G-code data. A .gcode file may be created by a slicing program, which turns a CAD drawing into a string of code that a suitable 3D printer can understand. These are just some of the more common input file formats for 3D printers, however it should be clear that many further alternatives are available.

In some examples, depending on the orthodontic treatment device selected by the user, the format of the input file may be adapted. Some of the orthodontic treatment devices may be manufactured from metal, such as biocompatible metal alloys. Examples of suitable alloys may include stainless steel and titanium. Others of the orthodontic treatment devices may preferably be manufactured from biocompatible polymers. Depending on the material one 3D printing technique may be more suitable than another, and 3D printers selected for these different purposes may support different file formats. Yet further orthodontic treatment devices may be made from ceramic materials.

In some examples, rather than the computer system generating the 3D virtual model of teeth, a method may comprise receiving the virtual model of the patient's teeth. In these cases, the virtual model of the teeth may be generated elsewhere e.g. in another computer system or in another application.

In some examples, the method may further comprise virtually attaching the adapted or the predefined virtual orthodontic treatment device to the virtual model of the patient's teeth. In the virtual model, a connection may be made between some of the elements of the patient's virtual teeth and parts of the selected orthodontic treatment devices. These elements of the virtual teeth and the parts of the orthodontic treatment devices may thus move together in a simulation of the orthodontic treatment foresee by an orthodontist. Based on such a simulation, an orthodontist or other professional may further adapt the virtual orthodontic treatment device to finally arrive at the most appropriate design for the orthodontic treatment device(s) to be manufactured.

Even though so far the explanation has focused on the design and manufacture of a single orthodontic treatment device, it should be clear that multiple virtual orthodontic treatment devices may be visualized at the same time in relation with the virtual model of the patient's teeth. Also, multiple devices may be adapted and adjusted. In an example, multiple brackets may be selected by the professional and fitted to different teeth of the virtual model at the same time. Their relative dimensions, their characteristics and positions may be adjusted if desired based on an overview of the several devices that may be employed in a treatment at the same time.

Figure 4A:
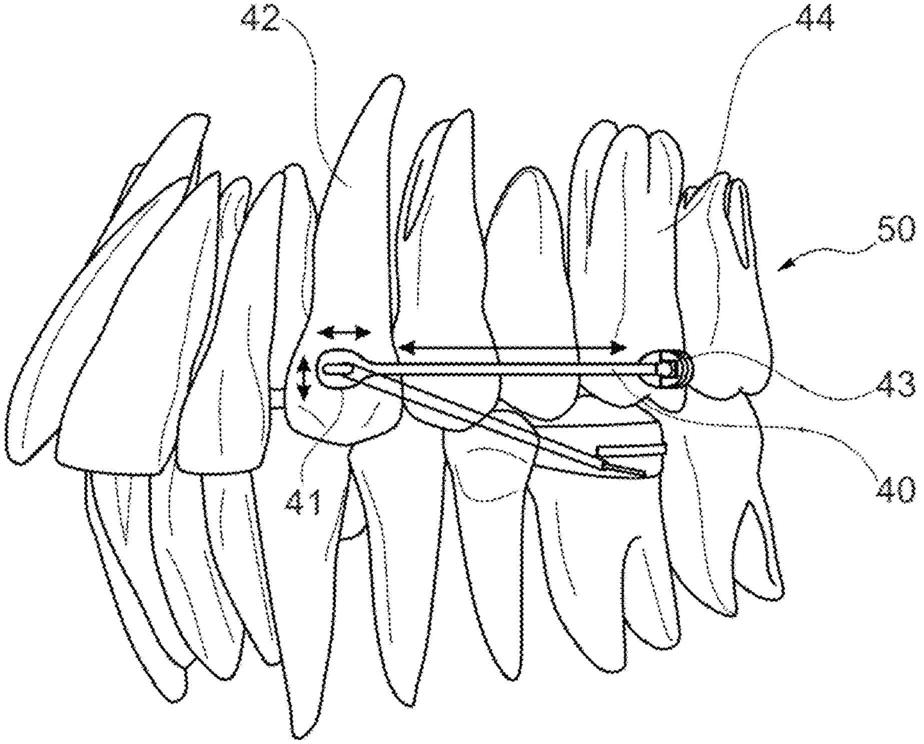
FIGS. 4A and 4B schematically illustrate a further example of a virtual orthodontic treatment device fitted to virtual teeth.

In examples, the methods may thus further comprise visualizing a second predefined virtual orthodontic treatment device on the display, adapting a characteristic of the second predefined virtual orthodontic treatment device in response to user input, and generating a second input file for a 3D printer based on the adapted second virtual orthodontic treatment device. FIG. 4A, which will be discussed in more detail later, schematically illustrates an example of a virtual orthodontic treatment device fitted to virtual teeth.

Figure 3:
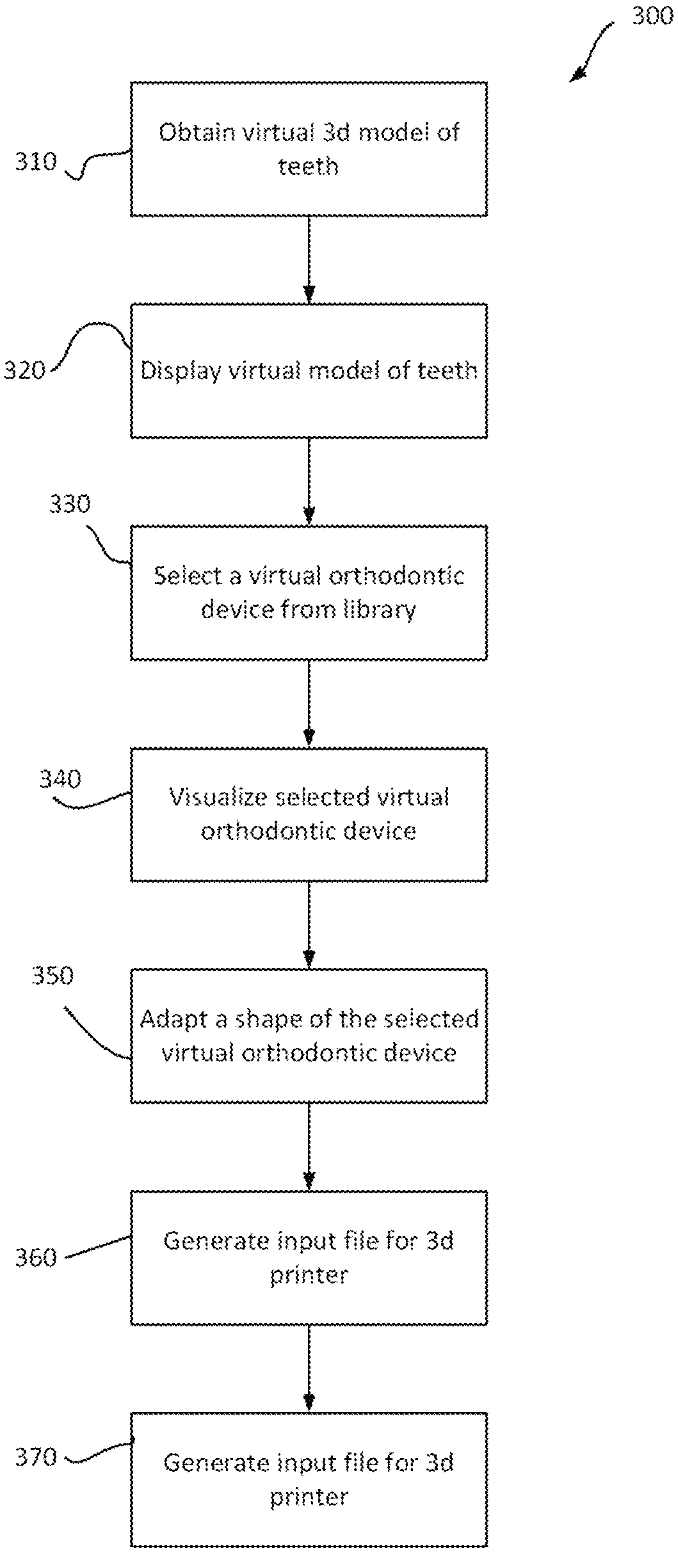
FIG. 3 schematically illustrates an example of a method for manufacturing an orthodontic treatment device.

FIG. 3 schematically illustrates an example of a method 300 for manufacturing an orthodontic treatment device. Such a method may be carried out by an orthodontist, or team of professionals in an orthodontal or dental clinic.

At block 310, a virtual 3D model of teeth may be obtained. Plaster models may form the basis for a 3D model, as well as images obtained by a 3D scanner, e.g. an intraoral scanner or cone beam ct scanner.

At block 320, the virtual model of the teeth may be shown on a suitable display. Based on the virtual 3D model, and possibly based on further in-person examination, a qualified professional may select an orthodontic treatment device that he/she deems suitable for the treatment of the individual patient at block 330. Such an orthodontic treatment device may be selected from a library or predefined orthodontic treatment devices.

At block 340, the selected virtual orthodontic treatment device may be visualized together with the virtual model of the teeth. As explained before, a professional may then customize the selected virtual orthodontic treatment device, at block 350. The whole or specifics parts of the virtual orthodontic treatment device may be adapted. Customizing may include e.g. one or more of: scaling (i.e. the virtual orthodontic model increases or decreases in all dimensions, optionally with the same scall in three dimensions), changing shapes, changing one or more objects or the relation between objects within the virtual orthodontic treatment device, adding or removing material, changing texture, locally changing dimensions and other.

At block 360, an input file for a 3D printer may be generated. A 3D printer may be directly coupled (with a cable or wirelessly) to a computer system running a suitable software. At block 370, the orthodontic treatment device designed for a specific patient may be 3D printed. The 3D printer may be physically located in the orthodontist or dental clinic or may be located remotely. In examples, a patient may not have to wait a day or a week or more to receive the orthodontic treatment devices specifically designed for him or her. Rather, the patient may leave the orthodontist clinic with the 3D printed devices already cemented on his/her teeth.

In some examples, 3D printing may comprise fused deposition modelling. In other examples, 3D printing may comprise direct metal laser sintering or electron beam melting. It should be clear that other techniques may be suitable as well. Depending on the materials used and depending on the device to be manufactured, one 3D technique may be favoured over another.

As already explained herein, adapting a shape of the selected virtual orthodontic treatment device may comprise virtually drawing on a display at least part of an outer shape of the virtual orthodontic treatment device. In further examples, other user input may be used, such as pop-up menus, and text input in which a professional may indicate certain dimensions, curvatures, positions, textures or other.

Both in the methods of FIGS. 2 and 3, it should be clear that the order of the blocks represented in the figure does not mean that these steps need to be or can only be carried out in a specific sequence. Rather, the order of the steps may be changed for several of the steps, and/or several steps may be carried out simultaneously. As noted before, specific steps described for a single virtual orthodontic treatment device may be repeated or simultaneously carried out for multiple virtual orthodontic treatment devices.

Before the design of an orthodontic treatment device is frozen and a 3D printer file is generated, an orthodontic treatment may be simulated in some examples. The way that multiple orthodontic treatment devices interact to cure a patient's specific malocclusion may be tested using finite element methods or similar. Based on such a simulation, the size of one or more orthodontic treatment devices may be changed, one or more devices may be fitted to different teeth, hooks or anchor points may be added etc. After the orthodontist is satisfied with the result, the orthodontic treatment devices may be manufactured. One or more input files for 3D printers may be generated for each of the orthodontic treatment devices.

Figure 4B:
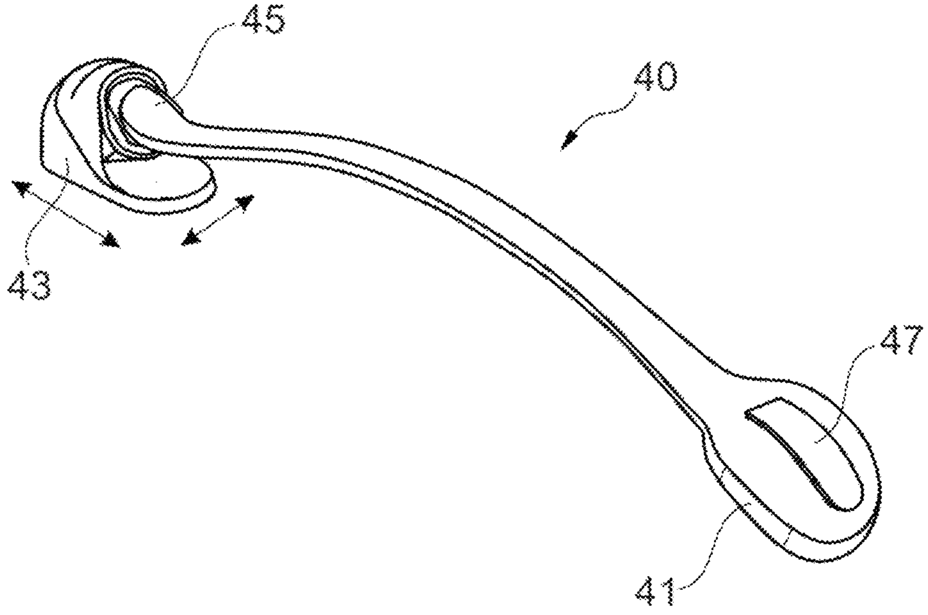

FIGS. 4A and 4B schematically illustrate a further example of a virtual orthodontic treatment device fitted to virtual teeth. In FIG. 4A, a distalizer 40 suitable for distalization or a posterior sector is shown in relation with a virtual model of a patient's teeth. More specifically, the distalizer shown in this example is a Carriere Motion™ distalizer.

Such a distalizer comprises a mesial bonding pad 41 which is configured to be fitted to a canine 42. The mesial bonding pad 41 may include a hook around which an elastic band may be fitted. The distalizer further comprises a molar bonding pad 43. An arm connects the mesial bonding pad 41 with the molar bonding pad. In the case of this specific distalizer, the arm may be integrally formed with the mesial bonding pad. The molar bonding pad comprises a receptacle to receive a distal portion of the arm. In this type of distalizer, the arm may an element allowing movement or rotation at the distal end of the arm, and in the case of the Carriere Motion™ distalizer, the arm may have a part-sphere at the end of the arm.

The receptacle and distal portion of the arm have precisely defined shapes that may define collision points between them. These collision points define stops to limit relative movement between the mesial bonding pad and the distal bonding pad. The stops may limit the rotation of the molar around its palatal root and the uprighting of the molar during the treatment. The ball-and-socket joint between arm and molar bonding pad may form part of a non-adaptable portion of the virtual distalizer. The precise definition of the collision points may be important in the treatment and therefore these elements, in examples, may be non-adaptable.

Other parts of the model such as length of the arm, and dimensions of the bonding pad(s) may be adapted by a user. In examples, also the location of the hook 47 on the mesial bonding pad 41 or on the arm connecting the mesial and molar bonding pads may be changed if so desired by the professional. Even multiple hooks might be selected for a specific malocclusion.

The hook 47 and/or the ball-and-socket joints may be defined as independent objects within the virtual model of the distalizer. A further independent object may be the arm connecting the mesial bonding bad 41 to the molar bonding pad 43. In examples, an orthodontics or other professional may then, through a suitable user interface, change the position of the virtual object "hook" with respect to the virtual object "arm". The size and shape of the hook may remain as original, simply the position of the whole object is redefined.

Adaptation of this specific virtual orthodontic treatment device may include one or more of the following: selection by a user of a mounting surface in the virtual model of the patient's teeth for the mesial bonding pad, selection of a mounting surface in the virtual model of the patient's teeth for the molar bonding pad, selection of a position of the hook, typing of a thickness of the arm connecting the mesial and molar bonding pads.

Additional input might include an orthodontist drawing an additional element, wing, hook, opening, or other in accordance with his/her devised treatment plan.

A computer (software) may, based on such data, calculate inter alia, a suitable length for the arm connecting mesial and molar bonding pads, a required curvature and size for the base surfaces of the mesial and molar bonding pads and other.

Figure 5A:
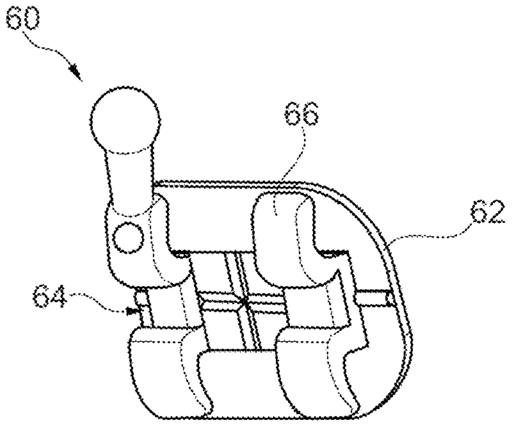
FIGS. 5A and 5B schematically illustrate a virtual model of other examples of orthodontic treatment devices, namely an orthodontic bracket and a buccal tube.
Figure 5B:
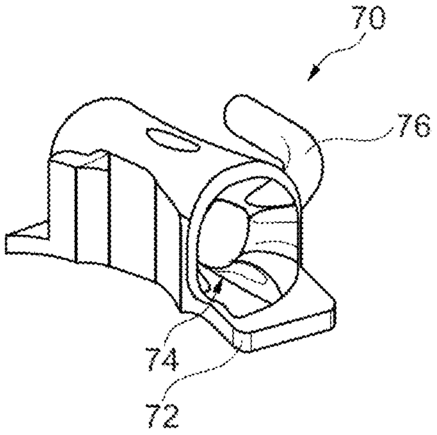

FIGS. 5A and 5B schematically illustrate yet further examples of virtual models of orthodontic treatment devices. Herein an orthodontic bracket 60 and a molar tube 70 have been schematically indicated.

Elements of the virtual model that an orthodontist may want to adapt to the specific tooth or malocclusion of a patient in case of an orthodontic bracket 60 include e.g. dimensions, and the mounting surface 62, or the curvature of the mounting surface 62 of the brackets, and the inclination of the archwire slot 64, location and size of wings 66 (if present). By choosing a suitable inclination of the archwire slot 64, the amount of torque applied to individual teeth may be adapted.

Elements of the virtual model that an orthodontist may want to adapt to a specific patient in the case of a buccal tube 70 may include, a location of a hook 76, a curvature and dimensions of the mounting surface 72. A library may include buccal tubes adapted for different archwires, so that a starting point for the orthodontist might be a buccal tube having an archwire slot 74 suitable for the foreseen archwire, and this virtual buccal tube may then be adapted through input from the orthodontist so that it is customized to the specific patient and/or treatment. Parameters that may be adapted may include an occlusal-gingival height, an in-out height, a mesial-distal base radius, an occlusal-gingival base radius, a type of hook, a presence of a hook, a location of a hook.

Examples of the methods disclosed herein may be implemented with hardware, software, firmware and combinations thereof.

Those of skill in the art would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application.

The various illustrative logical blocks, modules, and circuits described in connection with the disclosure herein may be implemented or performed with one or more general-purpose processors, a digital signal processor (DSP), cloud computing architecture, an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The computer program may be in the form of source code, object code, a code intermediate source and object code such as in partially compiled form, or in any other form suitable for use in the implementation of the processes. The carrier may be any entity or device capable of carrying the computer program.

If implemented in software/firmware, the functions may be stored on or transmitted over as one or more instructions or code on a computer-readable medium. Computer-readable media includes both computer storage media and communication media including any medium that facilitates transfer of a computer program from one place to another.

A storage media may be any available media that can be accessed by a general purpose or special purpose computer. By way of example, and not limitation, such computer-readable media can comprise RAM, ROM, EEPROM, CD/DVD or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor.

Also, any connection is properly termed a computer-readable medium. For example, if the software/firmware is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

For completeness, a number of aspects of the present disclosure are set out in the following numbered clauses:

Clause 1. A computer implemented method for generating an input file for a 3D printer, the method comprising:

- visualizing a virtual model of a patient's teeth on a display;
- visualizing a predefined virtual orthodontic treatment device on the display; and
- adapting a shape of the predefined virtual orthodontic treatment device in response to user input; and
- generating an input file for a 3D printer based on the adapted virtual orthodontic treatment device.

Clause 2. The method according to clause 1, wherein the predefined virtual orthodontic treatment device is selected from a library of predefined virtual orthodontic treatment devices.

Clause 3. The method according to clause 1, wherein the library of predefined virtual orthodontic treatment devices comprises one or more of: orthodontic brackets, Carriere Motion™ appliances, distalizers, expanders, Herbst® appliance, retainer, separators, distal jet appliance, and bite plates.

Clause 4. The method according to any of clauses 1-3, wherein the predefined virtual orthodontic treatment devices comprise an adaptable portion which can be adapted in response to user input, and a less adaptable portion.

Clause 5. The method according to clause 4, wherein the less adaptable portion is a non-adaptable portion which cannot be adapted in response to user input.

Clause 6. The method according to clause 4, wherein the less adaptable portion comprises a non-adaptable portion which cannot be adapted in response to user input and a portion which can be adapted to a limited extent in response to user input.

Clause 7. The method according to clause 5 or 6, wherein the non-adaptable portion comprises a joint, and/or an active element of the orthodontic treatment device.

Clause 8. The method according to any of clauses 4-7, wherein the adaptable portion comprises one base or two or more bases for anchoring the orthodontic treatment device to the patient's mouth, and/or a connector.

Clause 9. The method according to any of clauses 4-8, wherein predefined virtual orthodontic treatment devices configured to be bonded to one or more teeth of a patient are configured to be adapted in an occlusal-gingival plane and or a mesial-distal plane, and are configured not to be adapted in a buccal-lingual plane.

Clause 10. The method according to any of clauses 1-9, wherein the input file for the 3D printer is in one of the following formats: .stl, .obj, .gcode, .amf, .vrml, .ply, .fbx, .3mf.

Clause 11. The method according to any of clause 1-10, further comprising receiving the virtual model of the patient's teeth.

Clause 12. The method according to any of clauses 1-10, further comprising generating the virtual model of the patient's teeth.

Clause 13. The method according to any of clauses 1-12, wherein the virtual model of the patient's teeth is derived from images made by an intraoral scanner.

Clause 14. The method according to any of clauses 1-13, further comprising sending the input file to a 3D printer.

Clause 15. The method according to any of clauses 1-14, further comprising virtually attaching the adapted or the predefined virtual orthodontic treatment device to the virtual model of the patient's teeth.

Clause 16. The method according to clause 15, further comprising simulating an orthodontic treatment based on the use of the adapted virtual orthodontic treatment device, and optionally wherein simulating the orthodontic treatment includes using a finite element method.

Clause 17. The method according to any of clauses 1-16, further comprising:

- visualizing a second predefined virtual orthodontic treatment device on the display; and
- adapting a characteristic of the second predefined virtual orthodontic treatment device in response to user input; and
- generating a second input file for a 3D printer based on the adapted second virtual orthodontic treatment device.

Clause 18. The method according to any of clauses 1-17, wherein adapting the shape of the predefined virtual orthodontic treatment device is at least partially based on the virtual model of the patient's teeth.

Clause 19. The method according to clause 18, wherein the user input for adapting the shape of the predefined virtual orthodontic treatment device includes a selection of a point, surface or line of the virtual model of the patient's teeth.

Clause 20. A computer program comprising instructions which, when the program is executed by a computer, cause the computer to carry out the method of any of clauses 1-19.

Clause 21. A computer readable medium having stored thereon the computer program according to clause 20.

Clause 22. A carrier signal carrying the computer program according to clause 20.

Clause 23. A computing system comprising:

a module for visualizing a virtual model of a patient's teeth on a display;

a module for visualizing a predefined virtual orthodontic treatment device on the display;

a module for adapting a shape of the predefined virtual orthodontic treatment device in response to user input; and a module for generating an input file for a 3D printer based on the adapted virtual orthodontic treatment device.

Clause 24. The computing system according to clause 23, further comprising a memory having stored therein a library of predefined virtual orthodontic treatment devices.

Clause 25. The computing system according to any of clauses 23 or 24, further comprising a module for sending the input file to a 3D printer.

Clause 26. The computing system according to any of clauses 23-25, further comprising a module for virtually attaching the adapted or the predefined virtual orthodontic treatment device to the virtual model of the patient's teeth.

Clause 27. The computing system according to clause 26, further comprising a module simulating an orthodontic treatment based on the use of the adapted virtual orthodontic treatment device.

Clause 28. A computer system comprising:

a memory and a processor, wherein the processor is configured to carry out the method according to any of clauses 1-19.

Clause 29. The computer system according to any of clauses 23-28, further comprising a display.

Clause 30. A method for manufacturing an orthodontic treatment device comprising:

obtaining a virtual model of a patient's teeth;

displaying the virtual model of the patient's teeth on a display;

selecting a virtual orthodontic treatment device from a library of predefined virtual orthodontic treatment devices and visualizing the selected virtual orthodontic treatment device on the display;

adapting a shape of the selected virtual orthodontic treatment device to adapt to the virtual model of the patient's teeth;

generating an input file for a 3D printer based on the adapted virtual orthodontic treatment device; and 3D printing the orthodontic treatment device according to the generated input file.

Clause 31. The method according to clause 30, wherein 3D printing comprises fused deposition modelling.

Clause 32. The method according to clause 30 or 31, wherein 3D printing comprises direct metal laser sintering or electron beam melting.

Clause 33. The method according to any of clauses 30-32, wherein obtaining the virtual model of the patient's teeth comprises using an intraoral scanner coupled to a computing system.

Clause 34. The method according to any of clauses 30-33, wherein a user input for adapting the shape of the selected virtual orthodontic treatment device to the virtual model of the patient's teeth includes a selection of one or more of a point, a line, or a surface of the virtual model of the patient's teeth.

Clause 35. The method according to any of clauses 30-34, wherein adapting a shape of the selected virtual orthodontic treatment device comprises virtually drawing on a display at least part of an outer shape of the virtual orthodontic treatment device.

Clause 36. The method according to any of clauses-30-35, wherein the library of predefined virtual orthodontic treatment devices comprises one or more of: orthodontic brackets, distalizers, Carriere Motion™ distalizers, expanders, Herbst® appliance, retainer, lingual arch, transpalatal arch, separators, distal jet appliance, and bite plates.

Clause 37. The method according to any of clauses 30-36, wherein the predefined virtual orthodontic treatment devices in the library are partly customizable.

Clause 38. The method according to any of clauses 30-37, wherein the predefined virtual orthodontic treatment devices comprise an adaptable portion which can be freely adapted in response to user input, and a less adaptable portion which can be adapted to a limited extent in response to user input.

Clause 39. The method according to any of clauses 30-37, wherein the predefined virtual orthodontic treatment devices comprise an adaptable portion, a less adaptable portion and a non-adaptable portion.

Clause 40. The method according to any of clauses 30-37, wherein the predefined virtual orthodontic treatment devices comprise an adaptable portion which can be adapted in response to user input, and a non-adaptable portion which cannot be adapted in response to user input.

Clause 41. The method according to clause 39 or 40, wherein the non-adaptable portion comprises a joint, and/or an active element of the orthodontic treatment device.

Clause 42. The method according to any of clauses 39-41, wherein the non-adaptable portion comprises a base for anchoring the orthodontic treatment device to the patient's mouth, and/or a connector.

Clause 43. The method according to any of clauses—38-42, wherein predefined virtual orthodontic treatment devices configured to be bonded to one or more teeth of a patient are configured to be adapted in an occlusal-gingival plane and or a mesial-distal plane, and are configured not to be adapted in a buccal-lingual plane.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. A computer implemented method for generating an input file for a three-dimensional (3D) printer, the method comprising:

visualizing a virtual model of a patient's teeth on a display;

visualizing a predefined virtual orthodontic treatment device on the display, wherein the predefined virtual orthodontic treatment device is selected from a library of predefined virtual orthodontic treatment devices; wherein the selected predefined virtual orthodontic treatment device comprises an adaptable portion which can be adapted in response to user input, a non-adaptable portion which cannot be adapted in response to user input and a partly adaptable portion which can only be partially adapted in response to user input, wherein the partly adaptable portion can only be scaled and/or rotated and/or repositioned with respect to other portions of the virtual orthodontic treatment device and the method further comprising:

adapting a shape of the predefined virtual orthodontic treatment device in response to user input and at least partially based on the virtual model of the patient's teeth to generate an adapted virtual orthodontic treatment device; and generating the input file for the 3D printer for 3D printing of the orthodontic treatment device, the input file being based on the adapted virtual orthodontic treatment device.

2. The method according to claim 1, wherein the non-adaptable portion comprises a joint.

3. The method according to claim 1, wherein the adaptable portion comprises a base for anchoring the orthodontic treatment device to the patient's mouth.

4. The method according to claim 1, wherein the predefined virtual orthodontic treatment device includes predefined separate virtual objects.

5. The method according to claim 4, wherein relative positions and/or orientations of the separate virtual objects within the predefined virtual orthodontic treatment device are adaptable according to user input.

6. The method according to claim 5, wherein the shape of one or more of the predefined virtual objects is not adaptable.

7. The method according to claim 1, wherein the input file for the 3D printer is in one of the following formats: .stl, .obj, .gcode, .amf, .vrml, .ply, .fbx, .3mf.

8. The method according to claim 1, further comprising receiving or generating the virtual model of the patient's teeth.

9. The method according to claim 1, wherein the virtual model of the patient's teeth is derived from images made by an intraoral scanner.

10. The method according to claim 1, wherein the user input for adapting the shape of the predefined virtual orthodontic treatment device includes a selection of a point, surface or line of the virtual model of the patient's teeth.

11. The method according to claim 1, further comprising virtually attaching the adapted or the predefined virtual orthodontic treatment device to the virtual model of the patient's teeth and simulating an orthodontic treatment based on the use of the adapted virtual orthodontic treatment device.

12. A computer system comprising:

a non-volatile memory and a processor, wherein the processor is configured to carry out the method according to claim 1.

13. The method according to claim 1, wherein the non-adaptable portion comprises an active element of the orthodontic treatment device.

14. The method according to claim 1, wherein the non-adaptable portion comprises a portion of the orthodontic treatment device which is to be manufactured with low tolerances.

15. The method according to claim 1, wherein the adaptable portion comprises one base or two or more bases for anchoring the orthodontic treatment device to the patient's mouth.

16. The method according to claim 1, wherein predefined virtual orthodontic treatment devices configured to be bonded to one or more teeth of a patient are configured to be adapted in an occlusal-gingival plane and or a mesial-distal plane, and are configured not to be adapted in a buccal-lingual plane.

* * * * *